US012797099B2

(12) United States Patent
Martin

(10) Patent No.: US 12,797,099 B2
(45) Date of Patent: Nov. 17, 2026

(54) SURGICAL INSTRUMENT HAVING A THENAR EMINENCE HANDLE AND METHOD FOR USE THEREOF

(71) Applicant: Thomas Logan Martin, Atlanta, GA (US)

(72) Inventor: Thomas Logan Martin, Atlanta, GA (US)

( * ) Notice: Subject to any disclaimer, the term of this patent is extended or adjusted under 35 U.S.C. 154(b) by 53 days.

(21) Appl. No.: 18/520,896

(22) Filed: Nov. 28, 2023

(65) Prior Publication Data

US 2024/0090910 A1 Mar. 21, 2024

Related U.S. Application Data

(62) Division of application No. 17/953,899, filed on Sep. 27, 2022, now Pat. No. 11,849,965.

(60) Provisional application No. 63/249,381, filed on Sep. 28, 2021.

(51) Int. Cl.
*A61B 17/28* (2006.01)
*A61B 17/3201* (2006.01)
*A61B 17/00* (2006.01)

(52) U.S. Cl.
CPC ...... *A61B 17/2841* (2013.01); *A61B 17/3201* (2013.01); *A61B 2017/0042* (2013.01)

(58) Field of Classification Search
CPC ............ A61B 17/2841; A61B 17/3201; A61B 2017/0042
USPC .............................................................. 606/1
See application file for complete search history.

(56) References Cited

U.S. PATENT DOCUMENTS 5,556,403 A 9/1996 Michalos
5,833,697 A 11/1998 Ludwick
6,129,740 A 10/2000 Michelson
8,057,499 B2 11/2011 Grayzel et al.
8,535,348 B1 9/2013 Alshemari
9,237,899 B2 1/2016 Ray
9,717,485 B1 * 8/2017 Doerr ..................... A61B 17/00
10,413,290 B1 9/2019 Robert, III
11,849,965 B2 * 12/2023 Martin ............... A61B 17/3201
2004/0035903 A1 2/2004 Michelson
2009/0112246 A1 4/2009 Weisshaupt et al.
2010/0168722 A1 * 7/2010 Lee .................... A61B 17/2909 606/1
2011/0213347 A1 * 9/2011 Lee ...................... A61B 1/0052 606/1
2017/0196572 A1 7/2017 Robinson et al.
(Continued)

*Primary Examiner* — Ahmed M Farah

(57) ABSTRACT

The present disclosure provides a surgical instrument comprising an instrument body with a distal end including a working portion, and a proximal end including a handle. The instrument body includes a first arm and a second arm that are pivotable relative to one another. Each of the first arm and the second arm having a handle portion of the handle and a portion of the working portion. And each of the handle portions of the first and second arms being configured to enable a user to control the instrument body and move the portions of the working portion of the first and second arms between opened and closed positions. The handle portion of the first arm having a thenar eminence contacting surface adapted to contact at least a portion of a thenar eminence of a hand of the user during use, and facilitate at least movement of the handle to move the working portion of the first and second arms from the open position to the closed position.

14 Claims, 7 Drawing Sheets

(56) References Cited

U.S. PATENT DOCUMENTS

| | | | | |
|---|---|---|---|---|
| 2017/0196582 | A1 | 7/2017 | Richter et al. | |
| 2017/0277109 | A1 | 9/2017 | Koyama | |
| 2017/0354401 | A1* | 12/2017 | Doerr | A61B 17/00 |

* cited by examiner

SURGICAL INSTRUMENT HAVING A THENAR EMINENCE HANDLE AND METHOD FOR USE THEREOF

This application is a divisional of U.S. Ser. No. 17/953,899, filed Sep. 27, 2022; which claims the benefit of U.S. Provisional Application No. 63/249,381 filed Sep. 28, 2021; which are hereby incorporated by reference.

FIELD

The present technology generally relates to surgical instruments and instrument handles designed for ergonomic use with a palming based technique.

BACKGROUND

The use of medical instruments designed to grasp, cut, or lock onto other objects is near universal in medical procedures performed today. Many of the tools used to complete these functions are generally composed of two handles, attached to two arms, meeting at a joint that progresses to a jaw designed for its appropriate function. The handles of these devices are generally designed as rings, where typically the thumb and either the third or fourth finger are expected to be placed to operate the instrument. Although these tools are designed with ring-handles that invite the placement of fingers, many physicians instead utilize a technique known as palming. Palming is a method in which a medical tool is grasped within the hand, and in which no fingers are placed through the ring-handles, thus moving the operators hand closer to the jaws of the instrument and increasing their fine motor control over the tool. However, the handles of most medical tools are not designed for this technique, and thus operators of these tools utilizing a palming technique are forced to creatively apply forces in unintuitive manners to use them. Therefore, there is a need for medical instruments and/or handles of instruments designed to be utilized in a method consistent with the prevailing palming technique.

SUMMARY

The techniques of this disclosure generally relate to surgical instruments having a handle adapted to cooperate with the thenar eminence and other portions of the hand using a palming like technique and method for use of such instruments.

In one aspect, the present disclosure provides a surgical instrument including an instrument body having a distal end and an opposite proximal end, the distal end including a working portion, the proximal end including a handle, the instrument body having a first side and an opposite second side between the distal end and proximal end; a first arm and a second arm being pivotally movable to one another, each of the first arm and the second arm having a handle portion of the handle and a portion of the working portion; each of the handle portions of the first and second arms being configured to enable a user to control the instrument body and move the portions of the working portion of the first and second arms between opened and closed positions, the closed position resulting in closing the portions of the working portion of the first and second arms upon material or an article; and the handle portion of the first arm having a thenar eminence contacting surface adapted to contact at least a portion of a thenar eminence of a hand of the user during use, the handle portion of the first arm having a portion extending from the thenar eminence on a palmar side of the hand up to a radial side of one of a first metacarpal of the hand or a proximal phalanx of a thumb of the user when the user's thenar eminence is placed against the first side of the instrument body, the handle portion of the first arm permitting the user to move the portions of the working portion from the closed position to the opened position by pressing the radial side of the first metacarpal away from the second portion of the handle.

In another aspect, the present disclosure provides a surgical instrument including an instrument body having a distal end and an opposite proximal end, the distal end including a working portion, the proximal end including a handle, the instrument body having a first side and an opposite second side between the distal end and proximal end; a first arm and a second arm being pivotally movable to one another, each of the first arm and the second arm having a handle portion of the handle and a portion of the working portion; each of the handle portions of the first and second arms being configured to enable a user to control the instrument body and move the portions of the working portion of the first and second arms between opened and closed positions, the closed position resulting in closing the portions of the working portion of the first and second arms upon material or an article; and the handle portion of the first arm having a thenar eminence contacting surface on the first side of the instrument body, the thenar eminence contacting surface extending away from the second side and having a first concave curvature toward the first side, the first concave curvature being configured to generally conform to a contour of a portion of a medial portion of the thenar eminence to a lateral portion of the thenar eminence, the thenar eminence contacting surface being adapted to permit the user to open the surgical instrument by moving the first metacarpal away from the second arm.

In yet another aspect, the present disclosure provides a surgical instrument including an instrument body having a distal end and an opposite proximal end, the distal end including a working portion, the proximal end including a handle, the instrument body having a first side and an opposite second side between the distal end and proximal end; a first arm and a second arm being pivotally movable to one another, each of the first arm and the second arm having a handle portion of the handle and a portion of the working portion, the portions of the working portion of the first arm and the second arm each forming a grasping jaw, each of the grasping jaws being pivotally movable relative to one another to enable grasping of one of material and an article between the grasping jaws; each of the handle portions of the first and second arms being configured to enable a user to control the instrument body and move the portions of the working portion of the first and second arms between opened and closed positions, the closed position resulting in closing the working portions of the first and second arms upon the material or the article; the handle portion of the first arm having a thenar eminence contacting surface on the first side of the instrument body, the thenar eminence contacting surface extending away from the second side and having a first concave curvature toward the first side, the first concave curvature being configured to generally conform to a contour of a portion of a medial portion of a thenar eminence to a lateral portion of the thenar eminence, the thenar eminence contacting surface having a second concave curvature extending over a radial side of one of a first metacarpal of a hand of the user or a proximal phalanx of a thumb of the user, the thenar eminence contacting surface being adapted to permit the user to open the surgical instrument by moving the first metacarpal away from the second arm; the handle portion of the second arm having a palmar contacting surface on the first side of the instrument body and at least one finger contacting surface on the second side of the instrument body, the finger contacting surface being configured as a plate, the finger contact surface permitting the user to grasp the instrument and facilitate relative movement between the first and second arms to open and close the instrument; and a ratcheted locking mechanism attached to the handle portions for holding the grasping jaws in the closed position, the ratcheted locking mechanism having a first ratchet arm extending from the handle portion of the first arm and a second ratchet arm extending from the handle portion of the second arm, the first ratchet arm and the second ratchet arm each having a cooperating ratchet surface adapted to engage one another so as to hold the surgical instrument in the closed position, and, when disengaged, from one another to permit the surgical instrument to be moved to the opened position.

In a further aspect, the present disclosure provides a method of using a surgical instrument including providing a surgical instrument having a first arm and a second arm pivotally movable to one another, each of the first arm and the second arm having a handle portion and a working portion with the working portions being proximate a distal end and the handle portions being proximate a proximal end of the instrument body, the handle portion of the first arm having a thenar eminence contacting surface and an extension extending from the thenar eminence contacting surface to extend from a thenar eminence on a palmar side of a hand of a user up to a radial side of one of a first metacarpal of the hand or a proximal phalanx of a thumb of the user when the user's thenar eminence is placed against a first side of the handle portion of the first arm, the handle portion of the second arm having a palmar contacting surface on a first side of the second arm and at least one finger contacting surface on a second side of the second arm, the surgical instrument having a ratcheted locking mechanism attached to the handle portions to hold the surgical instrument in a closed position, the ratcheted locking mechanism having a first ratchet arm extending from the handle portion of the first arm and a second ratchet arm extending from the handle portion of the second arm, the ratchet arms each having a cooperating ratchet surface adapted to engage one another so as to hold the surgical instrument in the closed position, and, when disengaged from one another to permit the surgical instrument to be moved to an opened position; grasping the surgical instrument so that the thenar eminence of the user is placed against the thenar eminence contacting surface and a palm of the user contacts the palmar contacting surface and at least one finger of the user contacts the at least one finger contacting surface; pressing the radial side of one of the first metacarpal of the hand or the proximal phalanx of the thumb of the user into contact with the extension of the handle portion of the first arm and away from the handle portion of the second arm to position the surgical instrument in the opened position; closing the working portions of the first and second arms upon material or an article by moving the handle portions toward one another to engage the cooperating ratchet surfaces to one another; opening the ratcheted locking mechanism by a combination of flexion of the at least one finger against the palmar contacting surface and thumb abduction against the thenar eminence contacting surface to facilitate relative movement between the first and second arms and disengagement the cooperating ratchet surfaces; and pressing the radial side of one of the first metacarpal of the hand or the proximal phalanx of the thumb of the user into contact with the extension of the handle portion of the first arm and away from the handle portion of the second arm to once again position the surgical instrument in the opened position.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
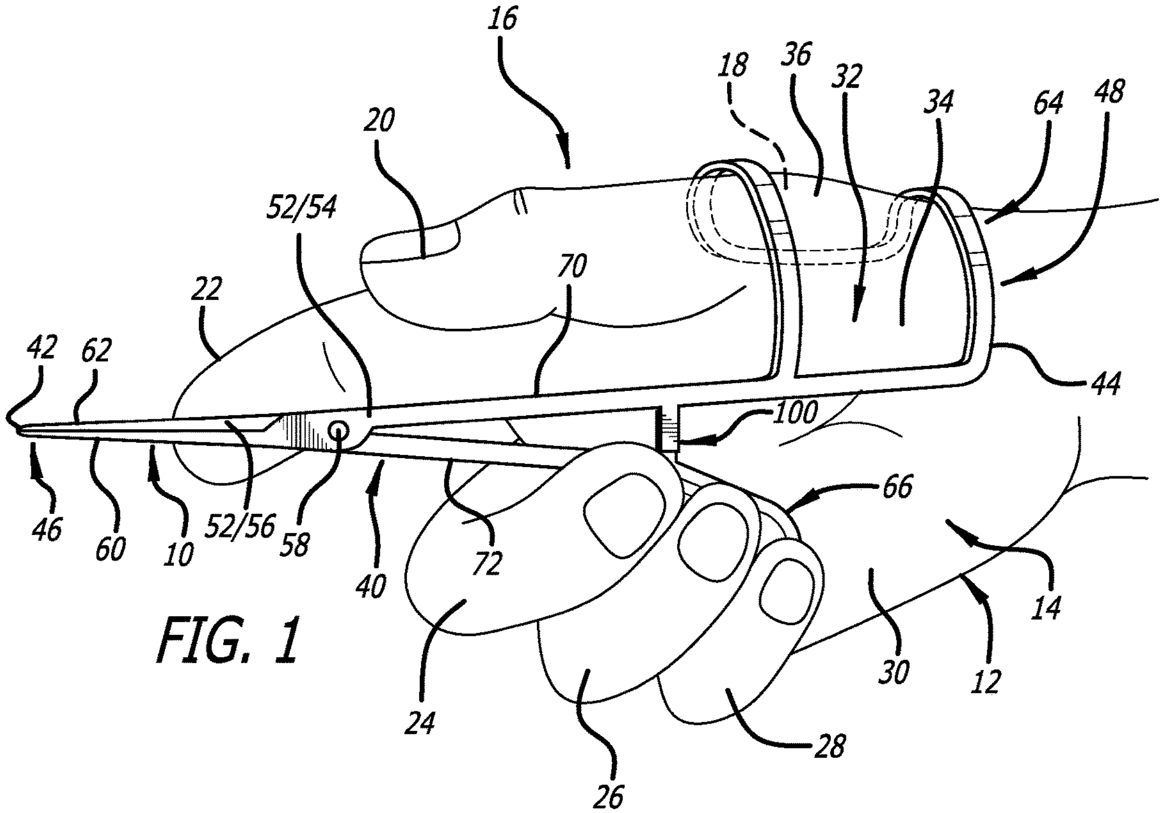
FIG. 1 is a side perspective view of a surgical instrument in a hand of a user according to a first embodiment of the present disclosure with a ratcheted locking mechanism engaged into a closed position.
Figure 2:
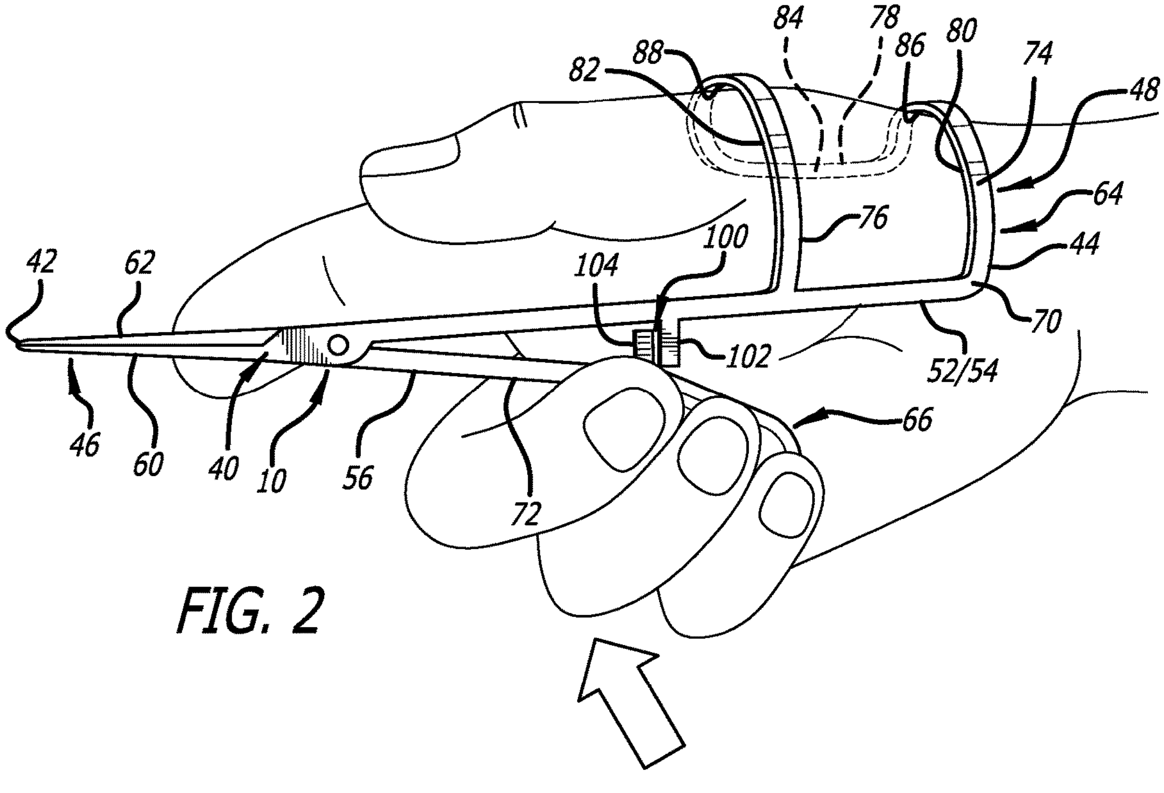
FIG. 2 is a side perspective view of the surgical instrument of FIG. 1 in the hand of the user with a ratcheted locking mechanism disengaged by the user.
Figure 3:
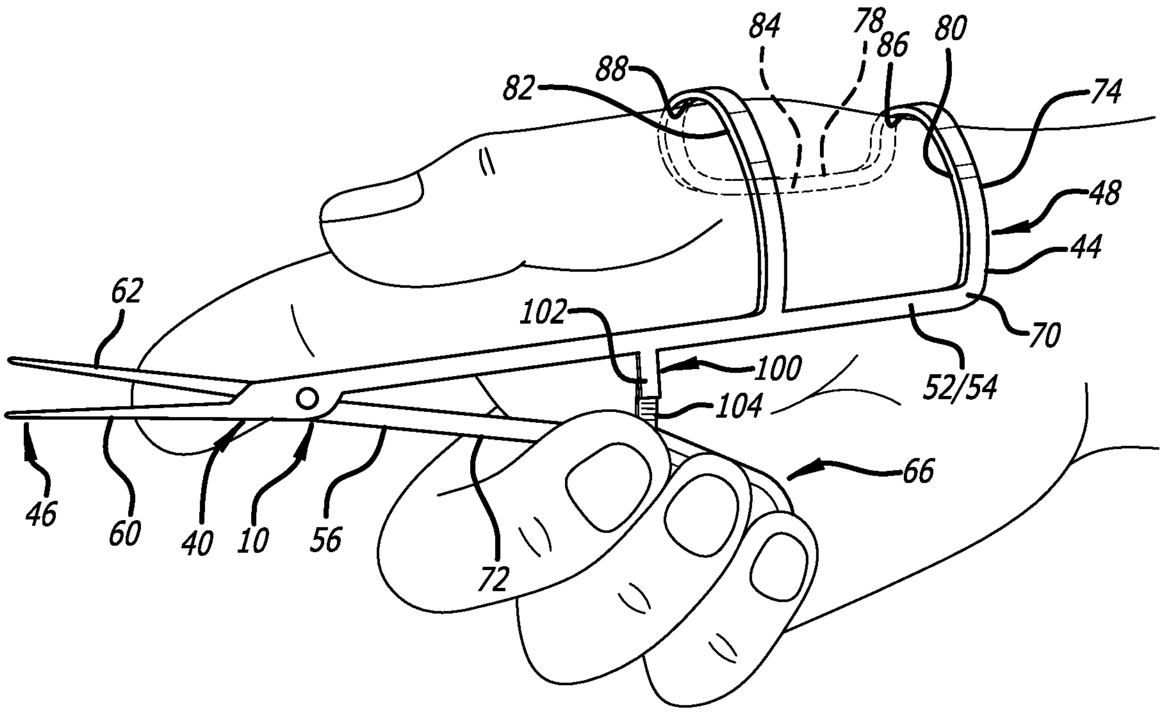
FIG. 3 is a side perspective view of the surgical instrument of FIG. 1 in the hand of the user with the surgical instrument moved to an open position by the user.

A surgical instrument according to an embodiment of the present disclosure is generally indicated by the numeral 10 in FIGS. 1-5. Depending on the configuration thereof, the surgical instrument 10 can be manipulated by a hand 12 of a user to, for example, clamp, grasp, grip, cut, and/or dissect an article or a material during surgery on a patient. Furthermore, the surgical instrument 10 of FIGS. 1-5, as well as surgical instruments of FIGS. 6-13, are depicted in right-hand configurations for manipulation by a right hand of the user, but it is noted that left-hand configurations that are mirror-images of the surgical instruments of FIGS. 1-13 also could be provided for manipulation by a left hand of the user. As depicted in FIGS. 1-3, the hand 12 of the user includes a palmar side 14, a radial side 16, and a dorsal side 18. The hand 12 includes a thumb 20, an index finger 22, a middle finger 24, a ring finger 26, and a pinky finger 28, and a palm 30 at the palmar side 14.

Furthermore, the palm 30, as depicted in FIG. 1, includes a thenar eminence 32, and the thenar eminence 32 includes a medial portion 34 and a lateral portion 36 on the palmar side 14. As discussed below, portions of the surgical instrument 10 are contactable to portions (including the medial portion 34 and/or the lateral portion 36) of the thenar eminence 32, as well as potentially portions of the radial side 16 and the dorsal side 18 of the hand 12. Furthermore, via such contact and via movement of a first metacarpal extending through the thenar eminence 32 and/or a proximal phalanx extending through the thumb 20, the surgical instrument 10 can be opened and closed.

Figure 4:
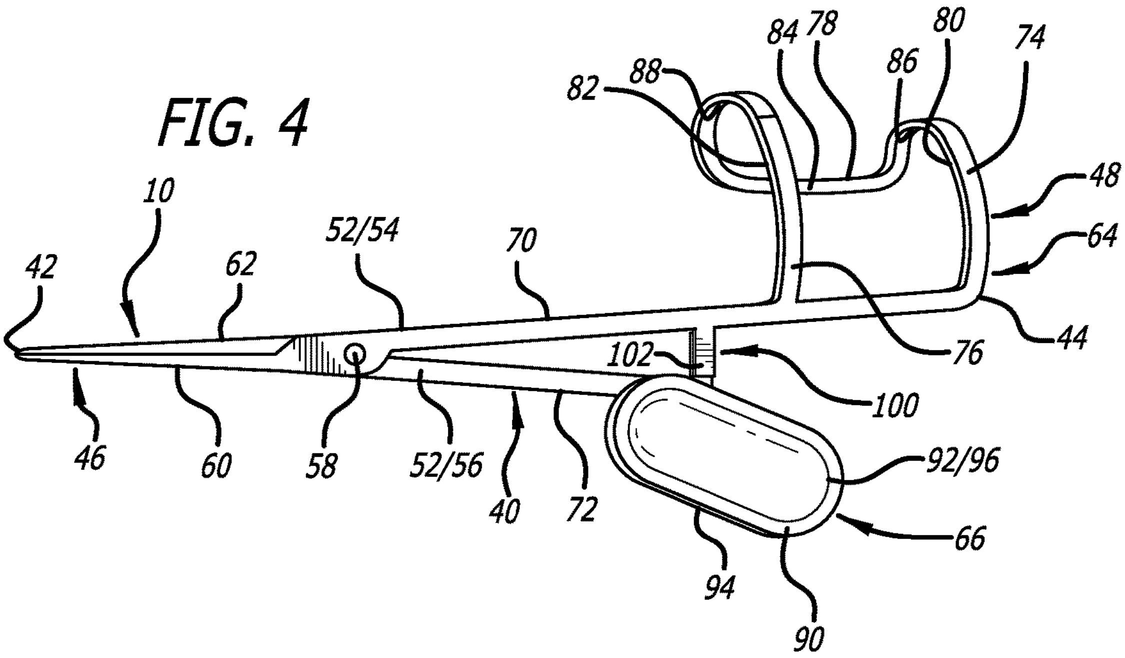
FIG. 4 is a side perspective view of the surgical instrument of FIG. 1 in the closed position.
Figure 5:
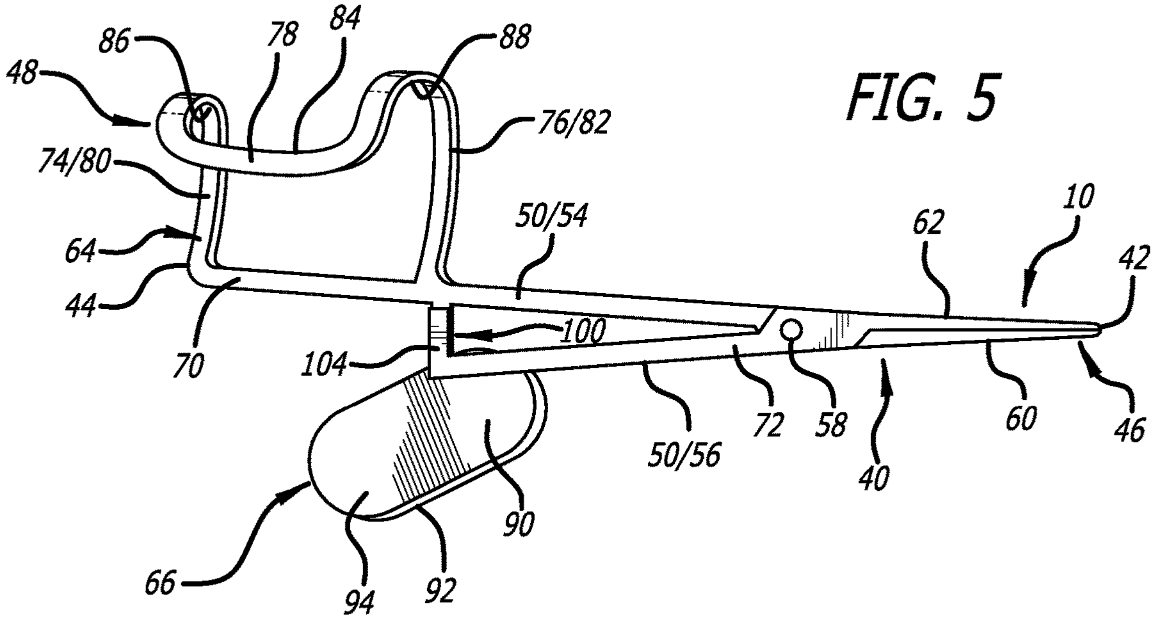
FIG. 5 is a side perspective view of the surgical instrument of FIG. 1 in the closed position shown from the opposite side of that show in FIG. 4.

As depicted in FIGS. 4 and 5, the surgical instrument 10 includes an instrument body 40 having a distal end 42 and an opposite proximal end 44. The distal end 42 includes a working portion 46 that facilitates grasping, griping, cutting, and/or dissecting, and the proximal end 44 includes a handle 48 facilitating control of the working portion 46 via manipulation by the hand 12 of the user. Furthermore, the instrument body 40 includes a first side 50 (FIG. 5) and an opposite second side 52 (FIG. 4), and a first arm 54 and a second arm 56 that are pivotally attached to one another at a pivotal connection 58.

As depicted in FIGS. 4 and 5, a first distal end portion 60 of the first arm 54 and a second distal end portion 62 of the second arm 56 adjacent the distal end 42 form portions of the working portion 46. And a first handle portion 64 and a second handle portion 66 of the handle 48 are formed by and/or attached to a first proximal end portion 70 and a second proximal end portion 72 of the first arm 54 and the second arm 56, respectively.

The first distal end portion 60 and the second distal end portion 62 forming the working portion 46 are moveable relative to one another between a closed position (FIGS. 1 and 2) and an opened position (FIG. 3) via manipulation of the handle 48 of the surgical instrument 10 by the user. The pivotal attachment of the first arm 54 and the second arm 56 affords plier/scissor-like movement of the first distal end portion 60 and the second distal end portion 62 relative to one another between the closed position and the opened position thereof via manipulation of the first handle portion 64 and the second handle portion 66 of the handle 48.

For example, each of the first distal end portion 60 and the second distal end portion 62 can form a grasping jaw that are pivotally moveable relative to one another in a plier-like fashion. Such grasping jaws can be used for clamping, grasping, and/or gripping at least one of an article or a material therebetween when moved from the opened position toward the closed position via manipulation of the handle 48. To illustrate, the grasping jaws via operation thereof can be used to grasp a needle, and/or can be used to grasp tissues of the patient. Furthermore, each of the first distal end portion 60 and the second distal end portion 62 instead can form a cutting blade that are pivotally moveable relative to one another in a scissor-like fashion. Such cutting blades can be used for cutting and/or dissecting an article or a material therebetween when moved from the opened position toward the closed position via manipulation of the handle 48. To illustrate, the cutting blades via operation thereof can be used to cut tissues of the patient during surgery.

As depicted in FIGS. 1-5, the first handle portion 64 of the handle 48 includes a portion of the first proximal end portion 70 of the first arm 54, a first C-shaped portion 74, a second C-shaped portion 76, and a U-shaped portion 78. The first C-shaped portion 74 is attached to the first proximal end portion 70 at a position adjacent the proximal end 44, the second C-shaped portion 76 is attached to the first proximal end portion 70 at a position between the distal end 42 and the proximal end 44, and the U-shaped portion 78 extends between the first C-shaped portion 74 and the second C-shaped portion 76. As depicted in FIGS. 1-3, the configuration of the first C-shaped portion 74, the second C-shaped portion 76, and the U-shaped portion 78 allows the first handle portion 64 to extend from the thenar eminence 32 of the hand 12 of the user on the palmar side 14 up to at least the radial side 16 of at least one of the first metacarpal of the hand 12 and the proximal phalanx of the thumb 20 when the user's thenar eminence 32 is placed against the first side 50 of the first arm 54. The first handle portion 64 can wrap around from the thenar eminence 32 on the palmar side 14 to the radial side 16 and then to the dorsal side 18 of the first metacarpal and/or the proximal phalanx.

The first handle portion 64 can be positioned at various locations along the first proximal end portion 70 to facilitate engagement with different portions of the hand 12. The first C-shaped portion 74 and the second C-shaped portion 76 can be positioned so that portions thereof and portions of the U-shaped portion 78 contact the radial side 14 of the first metacarpal of the hand 12, the radial side 14 of the proximal phalanx of the thumb 20, or the radial side 14 of portions of both the first metacarpal and the proximal phalanx. The first handle portion 64 permits the user to move the first distal end portion 60 and the second distal end portion 62 forming the portions of the working portion 46 from the closed position to the opened position by pressing thereagainst the radial side 16 of the first metacarpal and/or the proximal phalanx. And the first handle portion 64 also permits the user to move the first distal end portion 60 and the second distal end portion 62 forming the portions of the working portion 46 from the opened position to the closed position by pressing thereagainst portions of a medial portion and/or a lateral portion of the thenar eminence 32 on the palmar side 14.

The first C-shaped portion 74 includes a first hand-contacting surface in the form of a first thenar eminence contacting surface 80 and the second C-shaped portion 76 includes a second hand-contacting surface in the form of a second thenar eminence contacting surface 82. The first thenar eminence contacting surface 80 and the second thenar eminence contacting surface 82 extend away from the second side 52 and have a first concave curvature and a second concave curvature, respectively, toward the first side 50. The first concave curvature and the second concave curvature can include portions shaped to extend over, contact, cover, and generally conform to a contour of portions of the medial portion and/or the lateral portion of the thenar eminence 32. Furthermore, the first thenar eminence contacting surface 80 and the second thenar eminence contacting surface 82 can include a third concave curvature and a fourth concave curvature, respectively, with portions thereof that can extend over, contact, cover, and/or generally conform to the radial side 16 of the hand 12 over at least one of the first metacarpal and the proximal phalanx. And, the third concave curvature of the first thenar eminence contacting surface 80 and the fourth concave curvature of the second thenar eminence contacting surface 82 can include portions that can extend over, contact, and/or generally conform to the dorsal side 18 of the hand 12. A portion of the U-shaped portion 78 can include a dorsal contacting surface 84 that also can be configured to extend over, contact, and/or generally conform to the dorsal side 18 of the hand 12. The surfaces of the third concave curvature together with portions of the U-shaped portion 78 form a first transitional contacting surface 86, and the surfaces of the fourth concave curvature together with portions of the U-shaped portion 78 form a second transitional contacting surface 88 for contacting portions of the palmar side 14, the radial side 16, and/or the dorsal side 18 of the hand 12.

As depicted in FIGS. 4 and 5, the second handle portion 66 of the handle 48 includes a portion of the second proximal end portion 72 of the second arm 56 and a plate 90 attached to the second proximal end portion 72. The plate 90 can be attached relative to the first side 50 and/or the second side 52 of the second arm 56, or can be configured as two portions with the second proximal end portion 72 sandwiched therebetween. The plate 90, as depicted in FIGS. 4 and 5, is attached to second side 52 of the second proximal end portion 72. The plate 90 can include a finger-contacting surface 92 on one side thereof (FIG. 4) and an opposite palmar-contacting surface 94 on the other side thereof (FIG. 5). The finger-contacting surface 92 depicted in FIG. 5 faces the same direction as the first side 50, and the palmar-contacting surface 94 depicted in FIG. 4 faces the same direction as the second side 52. The finger-contacting surface 92 can include a depression 96 for receiving tips of one or more of the middle finger 24, the ring finger 26, and/or pinky finger 28 of the user. When the tips of the middle finger 24, the ring finger 26, and/or pinky finger 28 of the user are contacted to the finger-contacting surface 92, and the palm 30 of the user is contacted to the palmar-contacting surface 94, such contact can be used in conjunction with the above-discussed contact with the first handle portion 64 to move the working portion 46 from the closed position to the opened position, and vice versa.

Contact of the tips of at least one of the middle finger 24, the ring finger 26, and the pinky finger 28 with the finger-contacting surface 92 can also be used to move the second proximal end portion 72 of the second arm 54 inwardly toward the palmar side 14 relative to the first proximal end portion 70 of the first arm 54. In doing so, the tips of the middle finger 24, the ring finger 26, and/or the pinky finger 28 can be used, via flexion thereof, to press against the depression 96 to move the second proximal end portion 72 inwardly. Additionally, abduction of the thumb 20 can also be used to facilitate movement of the first proximal end portion 70 inwardly. As depicted in FIG. 2, inward movement can be used to release a locking mechanism 100. As depicted in FIGS. 1-5, the locking mechanism 100 can include a first arm portion 102 attached to the first proximal end portion 70 of the first arm 54, and a second arm portion 104 attached to the second proximal end portion 72 of the second arm 56. Each of the first arm portion 102 and the second arm portion 104 can include cooperating ratchet surfaces that, when engaged to one another, hold the working portion 46 in the closed position (FIG. 1), and when disengaged from one another (FIG. 2), permit the working portion 46 to be moved from the closed position to the opened position (FIG. 3). Normal plier/scissor-like movement of the first handle portion 64 and the second handle portion 66 to move the working portion 46 from the opened position to the closed position causes locking engagement of the ratchet surfaces of the first arm portion 102 and the second arm portion 104. The locking engagement of the ratchet surfaces of the first arm portion 102 and the second arm portion 104 then holds the working portion 46 in the closed position, as depicted in FIG. 1. In doing so, the clamping, the grasping, and/or the gripping of the article or the material by the working portion 46 can be maintained via the locking engagement. Furthermore, the inward movement of the second proximal end portion 72 relative to the first proximal end portion 70 of the first arm 54, via pressing against the finger-contacting surface 92 of the second handle portion 66 with the tips of the middle finger 24, the ring finger 26, and/or the pinky finger 28 and the abduction of the thumb 20, as depicted in FIG. 2, can be used to disengage the ratchet surfaces of the first arm portion 102 and the second arm portion 104 from one another to release the locking mechanism 100. The working portion 46, as depicted in FIG. 3, then can be moved from the closed position to the opened position in plier/scissor-like fashion with the ratchet surfaces of the first arm portion 102 and the second arm portion 104 disengaged from one another.

Figure 6:
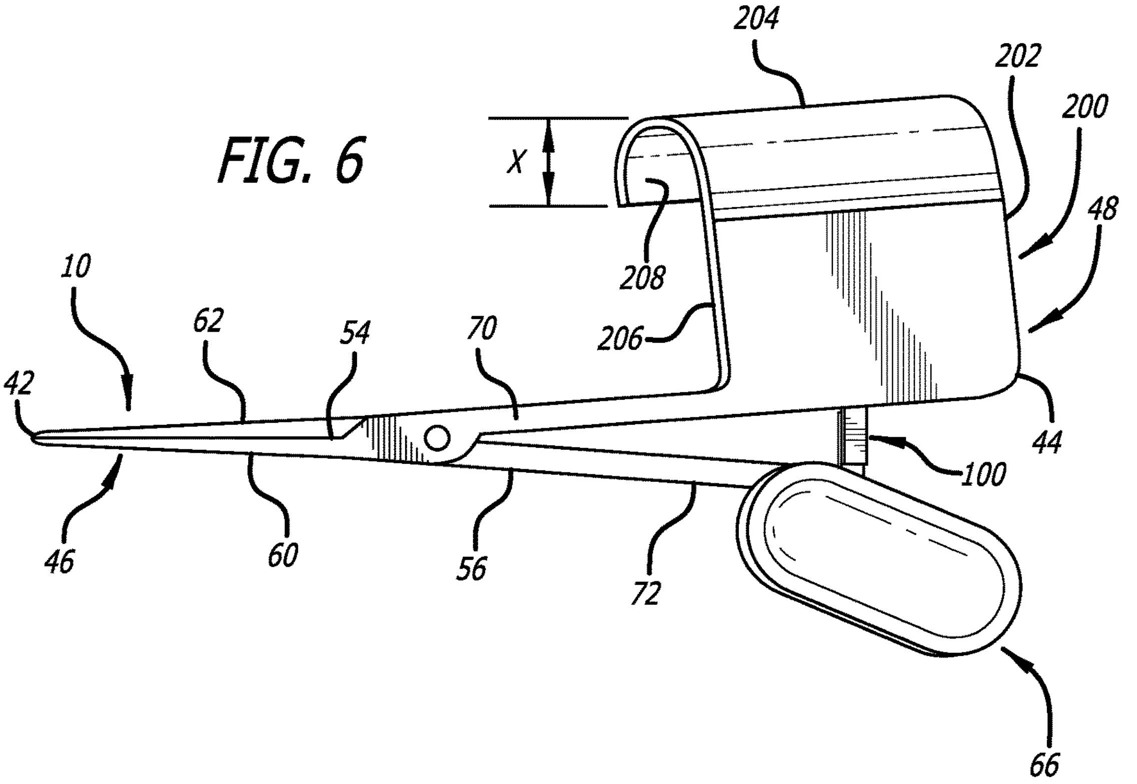
FIG. 6 is a side perspective view of a surgical instrument including a first alternative embodiment of a first handle portion depicted in a closed position.
Figure 7:
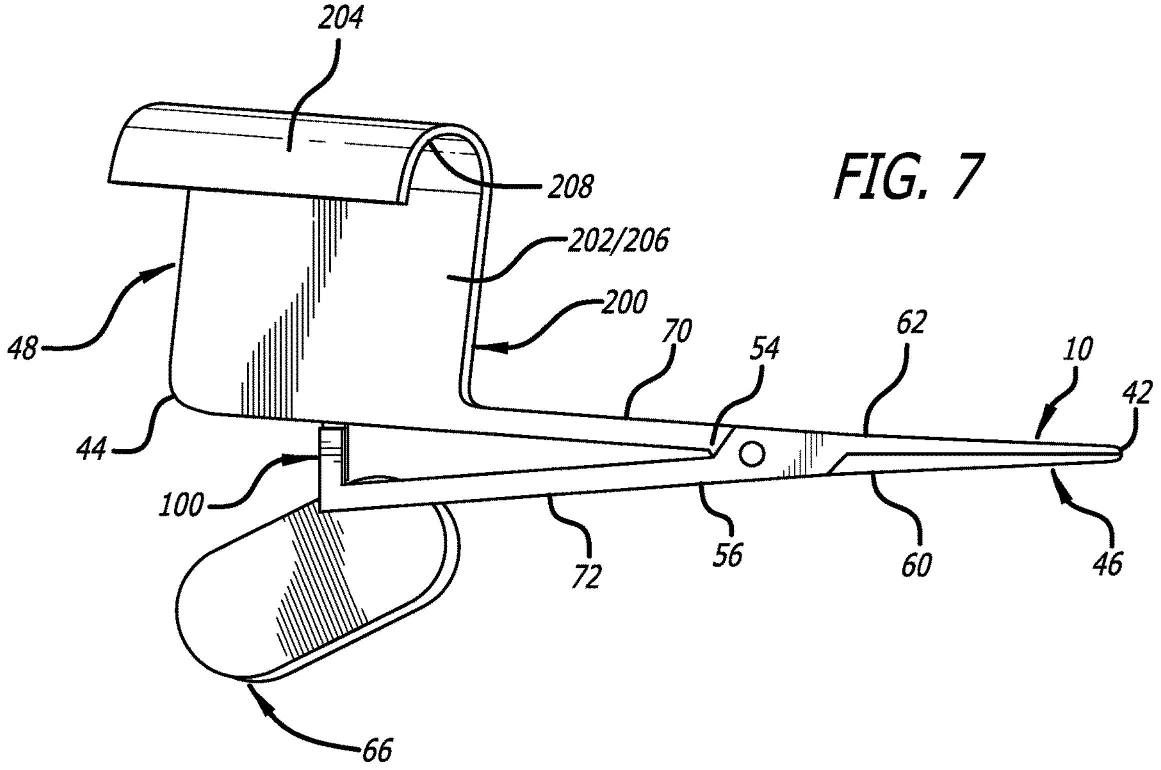
FIG. 7 is a side perspective view of the surgical instrument of FIG. 6 in the closed position shown from the opposite side of that show in FIG. 6.

Different alternate embodiments of a first handle portion are depicted in FIGS. 6-13. These different alternate embodiments of the first handle portion can be included on the surgical instrument 10. A first of the alternative embodiments of the first handle portion is generally indicated by the numeral 200 in FIGS. 6 and 7. The first handle portion 200 includes a portion of the first proximal end portion 70 of the first arm 54, a extension portion 202, and a extension portion 204. The extension portion 202 can be planar and is attached to and extends outwardly from the first proximal end portion 70, and the extension portion 204 can be cup-shaped and is attached to and extends outwardly from the planar extension portion 202. The configuration of the planar extension portion 202 and the cup-shaped extension portion 204 allows the first handle portion 200 to extend from the thenar eminence 32 of the hand 12 of the user on the palmar side 14 up to at least the radial side 16 of at least one of the first metacarpal of the hand 12 and the proximal phalanx of the thumb 20 when the user's thenar eminence 32 is placed against the first side 50 of the first arm 54. The first handle portion 200 can wrap around from the thenar eminence 32 on the palmar side 14 to the radial side 16 and then to the dorsal side 18 of the first metacarpal and/or the proximal phalanx. To that end, the planar extension portion 202 includes a thenar eminence contacting surface 206 that contacts, covers, and/or generally conforms to at least a portion of thenar eminence 32, and the cup-shaped extension portion 204 includes a transitional contacting surface 208 for contacting, covering, and/or generally conforming to portions of the palmar side 14, the radial side 16, and/or the dorsal side 18 of the hand 12. The cup-shaped extension portion 204, as depicted in FIGS. 6 and 7, is arcuate and defines an arcuate shape for the transitional contact surface 208. The cup-shaped extension portion 204 can extend upwardly from and then downwardly relative to the planar extension portion 202 through a distance X. The first handle portion 200 permits the user to move the first distal end portion 60 and the second distal end portion 62 forming the portions of the working portion 46 from the closed position to the opened position by pressing against the transitional contacting surface 208 with the radial side 16 of the first metacarpal and/or the proximal phalanx. And the first handle portion 200 also permits the user to move the first distal end portion 60 and the second distal end portion 62 forming the portions of the working portion 46 from the opened position to the closed position by pressing against the thenar eminence contacting surface 206 with portions of medial portion 34 and/or the lateral portion 36 of the thenar eminence 32 on the palmar side 14.

Figure 8:
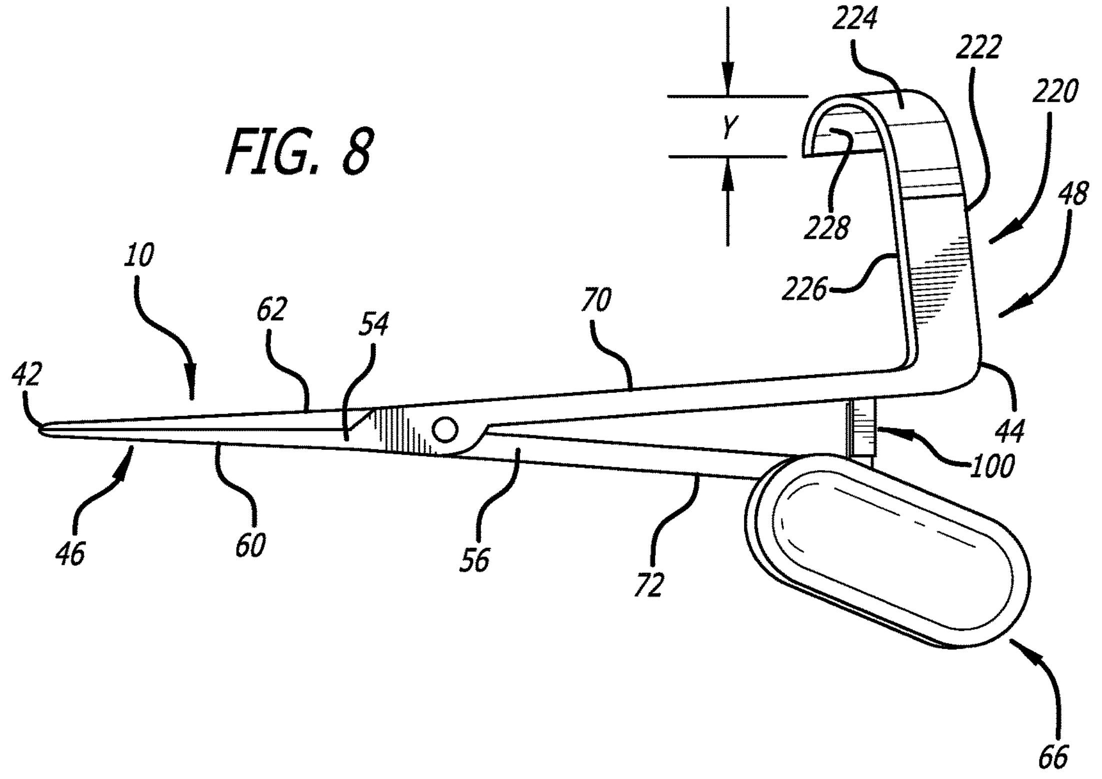
FIG. 8 is a side perspective view of a surgical instrument including a second alternative embodiment of a first handle portion depicted in a closed position.
Figure 9:
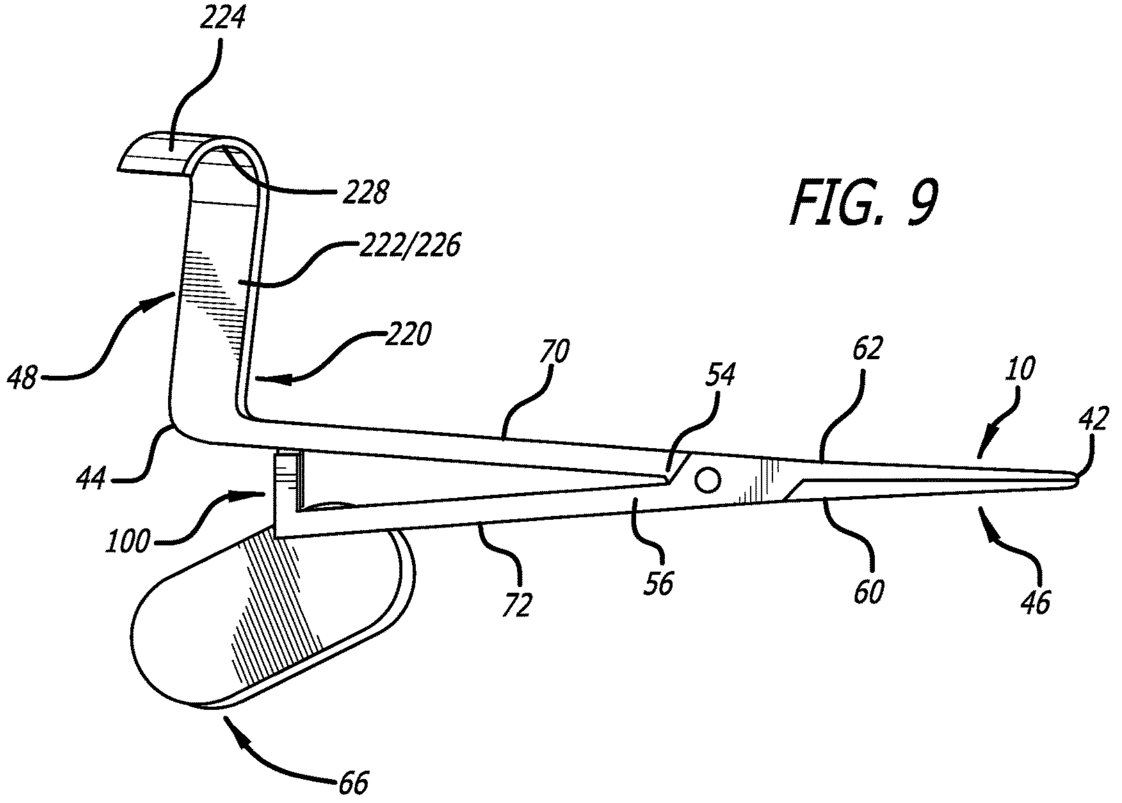
FIG. 9 is a side perspective view of the surgical instrument of FIG. 8 in the closed position shown from the opposite side of that show in FIG. 8.

A second of the alternative embodiments of the first handle portion is generally indicated by the numeral 220 in FIGS. 8 and 9. The first handle portion 220 includes a portion of the first proximal end portion 70 of the first arm 54, a extension portion 222, and a extension portion 224. The extension portion 222 can be planar, the extension portion 224 can be cup-shaped, and the planar extension portion 222 and the cup-shaped extension portion 224 are narrower than the planar extension portion 202 and the cup-shaped extension portion 204 of the first handle portion 200. The first handle portion 220 can be positioned at various locations along the first proximal end portion 70 to facilitate engagement with different portions of the hand 12. The first handle portion 220 can be positioned so that portions of the cup-shaped extension portion 224 can contact the radial side 14 of the first metacarpal of the hand 12, the radial side 14 of the proximal phalanx of the thumb 20, or the radial side 14 of portions of both the first metacarpal and the proximal phalanx. As depicted in FIGS. 8 and 9, the first handle portion 220 is positioned to facilitate contact of the cup-shaped extension portion 204 with at least the radial side 14 of the proximal phalanx. The planar extension portion 222 is attached to and extends outwardly from the first proximal end portion 70, and the cup-shaped extension portion 224 is attached to and extends outwardly from the planar extension portion 222. The configuration of the planar extension portion 222 and the cup-shaped extension portion 224 allows the first handle portion 220 to extend from the thenar eminence 32 of the hand 12 of the user on the palmar side 14 up to at least the radial side 16 of at least one of the first metacarpal of the hand 12 and the proximal phalanx of the thumb 20 when the user's thenar eminence 32 is placed against the first side 50 of the first arm 54. The first handle portion 220 can wrap around from the thenar eminence 32 on the palmar side 14 to the radial side 16 and then to the dorsal side 18 of the first metacarpal and/or the proximal phalanx. To that end, the planar extension portion 222 includes a thenar eminence contacting surface 226 that contacts, covers, and/or generally conforms to at least a portion of thenar eminence 32, and the cup-shaped extension portion 224 includes a transitional contacting surface 228 for contacting, covering, and/or generally conforming to portions of the palmar side 14, the radial side 16, and/or the dorsal side 18 of the hand 12. The cup-shaped extension portion 224, as depicted in FIGS. 8 and 9, is arcuate and defines an arcuate shape for the transitional contacting surface. The cup-shaped extension portion 224 can extend upwardly from and then downwardly relative to the planar extension portion 222 through a distance Y. The first handle portion 220 permits the user to move the first distal end portion 60 and the second distal end portion 62 forming the portions of the working portion 46 from the closed position to the opened position by pressing against the transitional contacting surface 228 with the radial side 16 of the first metacarpal and/or the proximal phalanx. And the first handle portion 220 also permits the user to move the first distal end portion 60 and the second distal end portion 62 forming the portions of the working portion 46 from the opened position to the closed position by pressing against the thenar eminence contacting surface 226 with portions of the medial portion 34 and/or the lateral portion 36 of the thenar eminence 32 on the palmar side 14.

Figure 10:
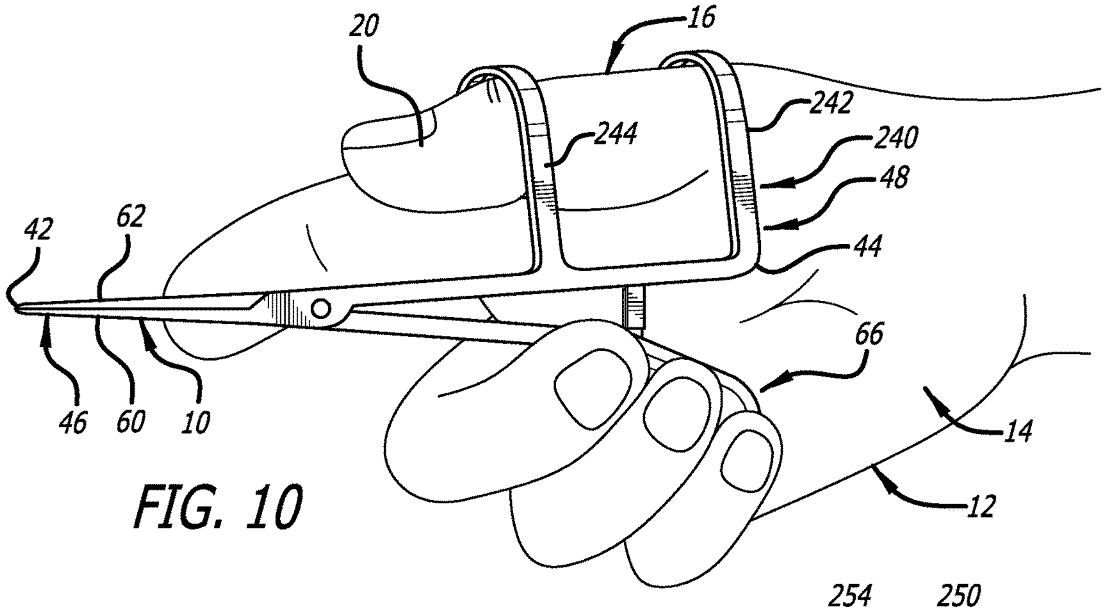
FIG. 10 is a side perspective view of a surgical instrument including a third alternative embodiment of a first handle portion depicted in a hand of a user and in a closed position.
Figure 11:
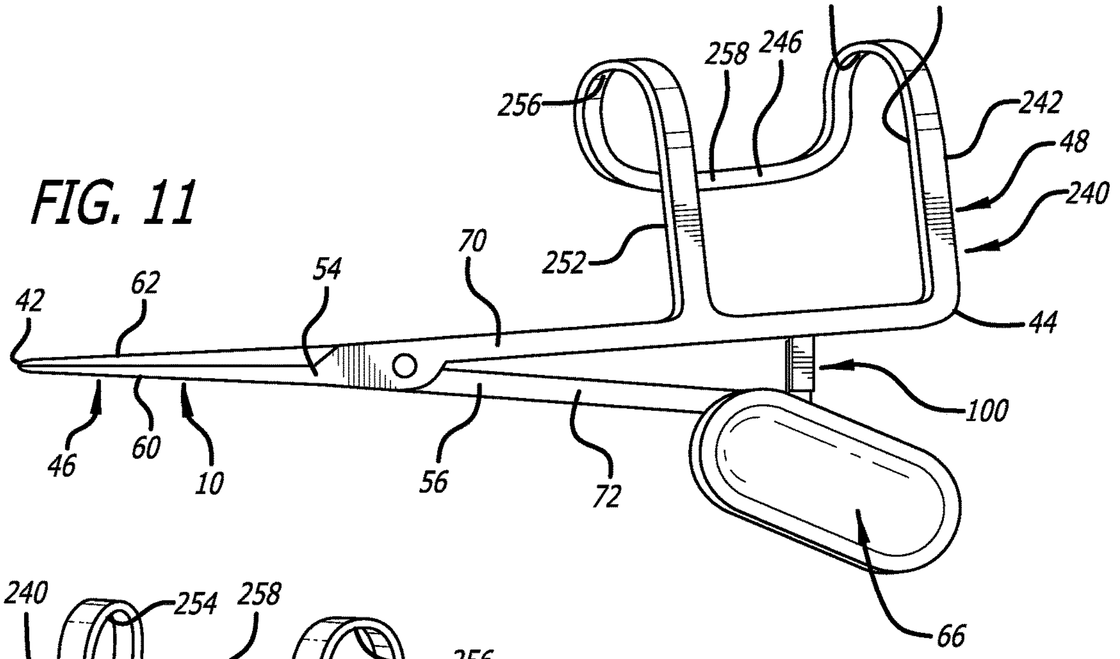
FIG. 11 is a side perspective view of the surgical instrument of FIG. 10 in the closed position.
Figure 12:
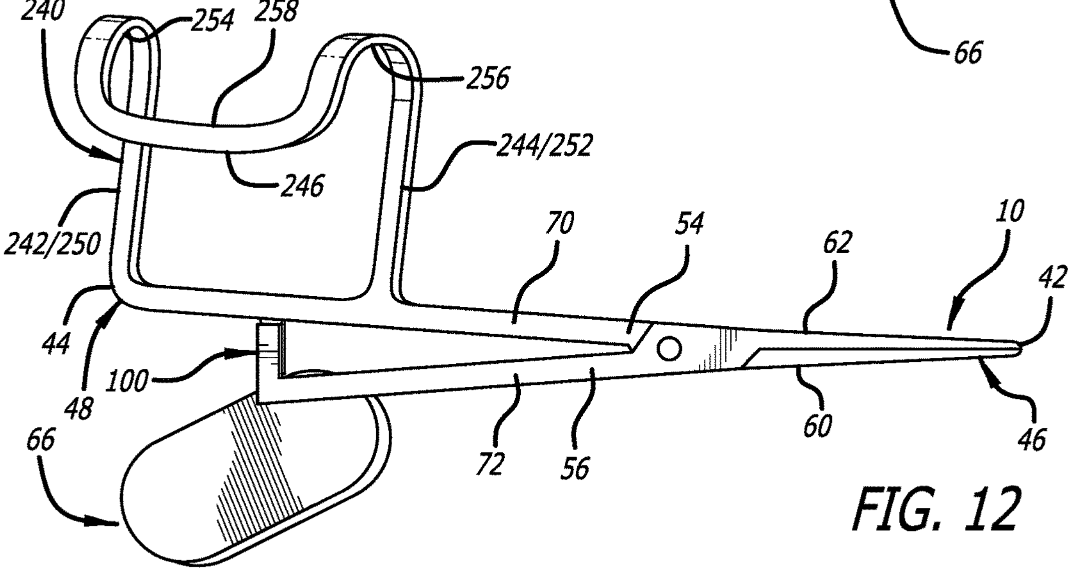
FIG. 12 is a side perspective view of the surgical instrument of FIG. 11 in the closed position shown from the opposite side of that show in FIG. 11.

A third of the alternative embodiments of the first handle portion is generally indicated by the numeral 240 in FIGS. 10-12. The first handle portion 240 includes a portion of the first proximal end portion 70 of the first arm 54, a first J-shaped portion 242 that is attached to and extends outwardly from the first proximal end portion 70 at a position adjacent the proximal end 44, a second J-shaped portion 244 that is attached to and extends outwardly from the first proximal end portion 70 at a position between the distal end 42 and the proximal end 44, and a U-shaped portion 246 that extends between the first J-shaped portion 242 and the second J-shaped portion 244. The first handle portion 240 can be positioned in various locations along the first proximal end portion 70. The first J-shaped portion 242 and the second J-shaped portion 244 can be positioned so that portions thereof and portions of the U-shaped portion 246 contact the radial side 14 of the first metacarpal of the hand 12, the radial side 14 of the proximal phalanx of the thumb 20, or the radial side 14 of portions of both the first metacarpal and the proximal phalanx. As depicted in FIGS. 10-12, the first handle portion 240 is positioned to facilitate contact of the first J-shaped portion 242, the second J-shaped portion 244, and the U-shaped portion 246 with at least the radial side 14 of the proximal phalanx. As such, the configuration of the first J-shaped portion 242, the second J-shaped portion 244, and the U-shaped portion 246 allows the first handle portion 240 to extend from the palmar side 14 of the hand 12 of the user up to at least the radial side 16 of at least one of the first metacarpal of the hand 12 and the proximal phalanx of the thumb 20 when portions of the user's palm 30 is placed against the first side 50 of the first arm 54. The first handle portion 240 can wrap around from the palmar side 14 to the radial side 16 and then to the dorsal side 18 of the first metacarpal and/or the proximal phalanx. To that end, the first J-shaped portion 242 and the second J-shaped portion 244 can include a first palmar contacting surface 250 and a second palmar contacting surface 252, respectively, for contacting, covering, and/or generally conforming to portions of the palmar side 14. Furthermore, the first J-shaped portion 242 together with the portions of the U-shaped portion 246 form a first transitional contacting surface 254, the second J-shaped portion 244 and portions of the U-shaped portion 246 form a second transitional contacting surface 256, and the U-shaped portion 246 includes a dorsal contacting surface 258 for contacting, covering, and/or generally conforming to portions of the palmar side 14, the radial side 16, and/or the dorsal side 18 of the hand 12. The first handle portion 240 permits the user to move the first distal end portion 60 and the second distal end portion 62 forming the portions of the working portion 46 from the closed position to the opened position by pressing against the transitional contacting surface 256 with the radial side 16 of the first metacarpal and/or the proximal phalanx on the radial side 16. And the first handle portion 240 also permits the user to move the first distal end portion 60 and the second distal end portion 62 forming the portions of the working portion 46 from the opened position to the closed position by pressing against the first palmar contacting surface 250 and the second palmar contacting surface 252 with portions of the palm 30.

Figure 13:
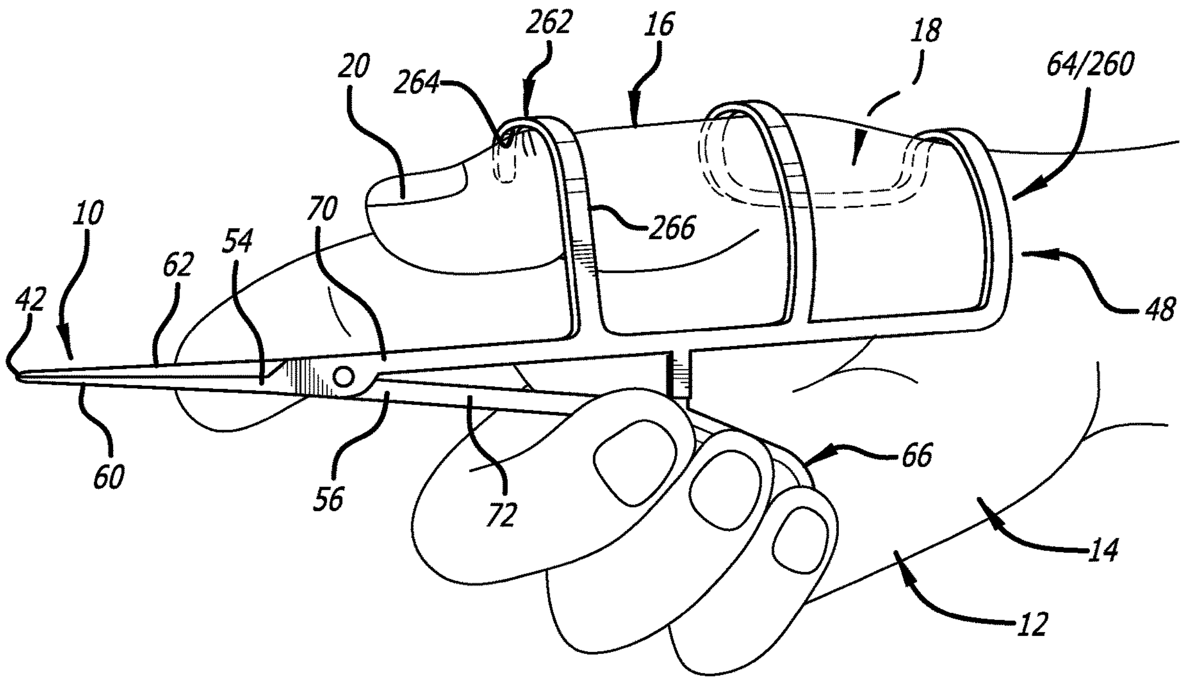
FIG. 13 is a side perspective view of a surgical instrument including a fourth alternative embodiment of a first handle portion depicted in a hand of a user and in a closed position.

A fourth of the alternative embodiments of the first handle portion is generally indicated by the numeral 260 in FIG. 13. The first handle portion 260 incorporates the first handle portion 64 and a secondary portion 262. The secondary portion 262 has a J-shape, and is attached to and extends outwardly from the first proximal end portion 70 at a position between the distal end 42 and the proximal end 44. Like the first handle portion 64, the secondary portion 260 can be positioned in various locations along the first proximal end portion 70. The secondary portion 262 can be positioned so that portions thereof contact the radial side 14 of the proximal phalanx and/or the distal phalanx of the thumb 20. As depicted in FIG. 13, the secondary portion 260 is positioned to facilitate contact with the radial side 14 of the proximal phalanx and the distal phalanx. As such, the configuration of the secondary portion 262 allows extension from the palmar side 14 of the hand 12 of the user up to at least the radial side 16 of the proximal phalanx and/or the distal phalanx of the thumb 20 when the user's thenar eminence 32 is placed against the first side 50 of the first arm 54. The secondary portion 262 can wrap around from the palmar side 14 to the radial side 16 and then to the dorsal side 18 of the proximal phalanx and/or the distal phalanx of the thumb 20. The secondary portion 262 can include a first thumb contacting surface 264 and a second thumb contacting surface 266 for contacting, covering, and/or generally conforming to portions of the palmar side 14, the radial side 16, and/or the dorsal side 18 of the hand 12. The first handle portion 260 including the secondary portion 262 permits the user to move the first distal end portion 60 and the second distal end portion 62 forming the portions of the working portion 46 from the closed position to the opened position by at least in part pressing against the first thumb contacting surface 264 with the radial side of the proximal phalanx and/or the distal phalanx of the thumb 20. And the first handle portion 260 including the secondary portion 262 also permits the user to move the first distal end portion 60 and the second distal end portion 62 forming the portions of the working portion 46 from the opened position to the closed position by at least in part pressing against the second thumb contacting surface 266 with the palmar side of the proximal phalanx and/or the distal phalanx of the thumb 20. Opening and closing of the working end 46 of the surgical instrument 10 including the first handle portion 260 can also be effectuated as described above using the first handle portion 64 incorporated therein. Furthermore, rather than incorporating the first handle portion 64, the secondary portion 262 could also be used by itself as the first handle portion 260 to facilitate opening and closing of the surgical instrument 10. To that end, opening and closing of the working end 46 would be effectuated by the above-described pressing of the proximal phalanx and/or the distal phalanx of the thumb 20 against the first thumb contacting surface 264 and the second thumb contacting surface 266.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A surgical instrument comprising:

an instrument body having a distal end and an opposite proximal end, the distal end including a working portion, the proximal end including a handle, the instrument body having a first side and an opposite second side between the distal end and proximal end;

a first arm and a second arm being pivotally movable to one another, each of the first arm and the second arm having a handle portion of the handle and a portion of the working portion;

each of the handle portions of the first and second arms being configured to enable a user to control the instrument body and move the portions of the working portion of the first and second arms between opened and closed positions, the closed position resulting in closing the portions of the working portion of the first and second arms upon material or an article; and the handle portion of the first arm having a thenar eminence contacting surface on the first side of the instrument body, the thenar eminence contacting surface extending away from the second side and having a first concave curvature toward the first side, the first concave curvature being configured to generally conform to a contour of a portion of a medial portion of the thenar eminence to a lateral portion of the thenar eminence, the thenar eminence contacting surface being adapted to permit the user to open the surgical instrument by moving a first metacarpal away from the second arm.

2. The surgical instrument of claim 1, wherein the thenar eminence contacting surface has a second concave curvature extending over a radial side of one of a first metacarpal of a hand of the user or a proximal phalanx of a thumb of the user.

3. The surgical instrument of claim 2, wherein the second concave curvature further extends to a dorsal side of the hand of the user.

4. The surgical instrument of claim 1, wherein the thenar eminence contacting surface has a cupping portion extending over one of the first metacarpal of the hand or a proximal phalanx of a thumb of the user.

5. The surgical instrument of claim 1, wherein the handle portion of the first arm is configured to contact at least a portion of the thenar eminence of the hand of the user, and being configured to wrap around from the thenar eminence on a palmar side of the hand up to a radial side of the first metacarpal of the hand of the user and to extend over at least a portion of a dorsal side of the first metacarpal.

6. The surgical instrument of claim 1, wherein the handle portion of the second arm has a palmar contacting surface on the first side of the instrument body and at least one finger contacting surface on the second side of the instrument body, the finger contacting surface being configured as a plate having at least one depression for receipt of a tip of at least one finger, the finger contacting surface permitting the user to grasp the instrument and facilitate relative movement between the first and second arms to open and close the instrument.

7. The surgical instrument of claim 1, further comprising a ratcheted locking mechanism attached to the handle portions for holding the portions of the working portion in the closed position, the ratcheted locking mechanism having a first ratchet arm extending from the handle portion of the first arm and a second ratchet arm extending from the handle portion of the second arm, the first ratchet arm and the second ratchet arm each having a cooperating ratchet surface adapted to engage one another so as to hold the surgical instrument in the closed position, and, when disengaged from one another, to permit the surgical instrument to be moved to the opened position.

8. The surgical instrument of claim 1, wherein the portions of the working portion of the first arm and the second arm each form a grasping jaw, each of the grasping jaws being pivotally movable relative to one another to enable grasping of one of the material and the article between the grasping jaws.

9. The surgical instrument of claim 8, wherein the surgical instrument is a surgical needle holder and the grasping jaws are configured to grasp a needle.

10. A surgical instrument comprising:

an instrument body having a distal end and an opposite proximal end, the distal end including a working portion, the proximal end including a handle, the instrument body having a first side and an opposite second side between the distal end and proximal end;

a first arm and a second arm being pivotally movable to one another, each of the first arm and the second arm having a handle portion of the handle and a portion of the working portion, the portions of the working portion of the first arm and the second arm each forming a grasping jaw, each of the grasping jaws being pivotally movable relative to one another to enable grasping of one of material and an article between the grasping jaws;

each of the handle portions of the first and second arms being configured to enable a user to control the instrument body and move the portions of the working portion of the first and second arms between opened and closed positions, the closed position resulting in closing the working portions of the first and second arms upon the material or the article;

the handle portion of the first arm having a thenar eminence contacting surface on the first side of the instrument body, the thenar eminence contacting surface extending away from the second side and having a first concave curvature toward the first side, the first concave curvature being configured to generally conform to a contour of a portion of a medial portion of a thenar eminence to a lateral portion of the thenar eminence, the thenar eminence contacting surface having a second concave curvature extending over a radial side of one of a first metacarpal of a hand of the user or a proximal phalanx of a thumb of the user, the thenar eminence contacting surface being adapted to permit the user to open the surgical instrument by moving the first metacarpal away from the second arm;

the handle portion of the second arm having a palmar contacting surface on the first side of the instrument body and at least one finger contacting surface on the second side of the instrument body, the finger contacting surface being configured as a plate, the finger contacting surface permitting the user to grasp the instrument and facilitate relative movement between the first and second arms to open and close the instrument; and a ratcheted locking mechanism attached to the handle portions for holding the grasping jaws in the closed position, the ratcheted locking mechanism having a first ratchet arm extending from the handle portion of the first arm and a second ratchet arm extending from the handle portion of the second arm, the first ratchet arm and the second ratchet arm each having a cooperating ratchet surface adapted to engage one another so as to hold the surgical instrument in the closed position, and, when disengaged, from one another to permit the surgical instrument to be moved to the opened position.

11. The surgical instrument of claim 10, wherein the second concave curvature further extends to a dorsal side of the hand of the user.

12. The surgical instrument of claim 10, wherein the thenar eminence contacting surface has a cupping portion extending over one of the first metacarpal of the hand or the proximal phalanx of the thumb of the user.

13. The surgical instrument of claim 10, wherein the handle portion of the first arm is configured to contact at least a portion of the thenar eminence of the hand of the user, and being configured to wrap around from the thenar eminence on a palmar side of the hand up to the radial side of the first metacarpal of the hand of the user and to extend over at least a portion of a dorsal side of the first metacarpal.

14. The surgical instrument of claim 10, wherein the surgical instrument is a surgical needle holder and the grasping jaws are configured to grasp a needle.

* * * * *